United States Patent [19]

Nobles

[11] Patent Number: 5,026,383
[45] Date of Patent: Jun. 25, 1991

[54] APPARATUS FOR IN-SITU CUTTING OF VALVES WITHIN VEINS AND METHOD THEREFOR

[76] Inventor: Anthony A. Nobles, 8686 Tern Ave., Fountain Valley, Calif. 92708

[21] Appl. No.: 366,427

[22] Filed: Jun. 14, 1989

[51] Int. Cl.⁵ .......................................... A61F 17/132
[52] U.S. Cl. .................................. 606/159; 606/170; 606/180
[58] Field of Search ............... 606/159, 167, 170, 179, 606/180, 183, 194; 604/22

[56] References Cited

U.S. PATENT DOCUMENTS

| | | | |
|---|---|---|---|
| 3,837,345 | 9/1974 | Matar | 606/159 |
| 4,175,545 | 11/1979 | Termanini | |
| 4,493,321 | 1/1985 | Leather | 606/159 |
| 4,528,982 | 7/1985 | Wellenstam | 606/159 |
| 4,574,781 | 3/1986 | Chin | 606/159 |
| 4,576,162 | 3/1986 | McCorkle | 606/159 |
| 4,655,217 | 4/1987 | Reed | 606/159 |
| 4,739,760 | 4/1988 | Chin et al. | |
| 4,768,508 | 9/1988 | Chin et al. | 606/159 |

FOREIGN PATENT DOCUMENTS

83/04174 12/1983 PCT Int'l Appl.

OTHER PUBLICATIONS

"In Situ Saphenous Vein Bypass: 1962 to 1987" by John E. Connolly, M.D., The American Journal of Surgery, Jul. 1987.
Instrumental Evolution of the Valve Incision Method of In Situ Saphenous Vein Bypass by Robert P. Leather, M.D., Dhiraj M. Shah, M.D., John D. Corson, M.D. and Allastair M. Karmody, M.D., Journal of Vascular Surgery, Jan. 1984.
Publication announcement: In Situ Bypass Grafting by Dr. LeMaitre.
Advertisement: Leather In Situ Valve Cutter Kit by American Hospital Supply Corp., Jun. 1985.
Advertisement: Hall Vein Stripper by Cabot Limited, Apr. 1986.
Sales Information: Vascutech, Inc.—The LeMaitre Valvulotome System, Jun. 1987.

Primary Examiner—Robert A. Hafer
Assistant Examiner—Kerry Owens
Attorney, Agent, or Firm—Knobbe, Martens, Olson & Bear

[57] ABSTRACT

An apparatus for in-situ cutting through one-way valves in a vein to convert the vein for use as an artery and a method therefor. The apparatus employs a cutting catheter and a pulling catheter. The pulling catheter is advanced through the vein in the normal direction of blood flow and is then connected to a cutting catheter and pulled back reversely through the one-way valves. The cutting catheter carries cutting blades which sever the valve cusps. The connection between the two catheters is effected by a filament which can be swiftly and readily connected to the pulling catheter. The cutting catheter employs a viewing scope which can be utilized to observe the valve cusps and align the cutting blades with the cusps to achieve effective cutting.

12 Claims, 2 Drawing Sheets

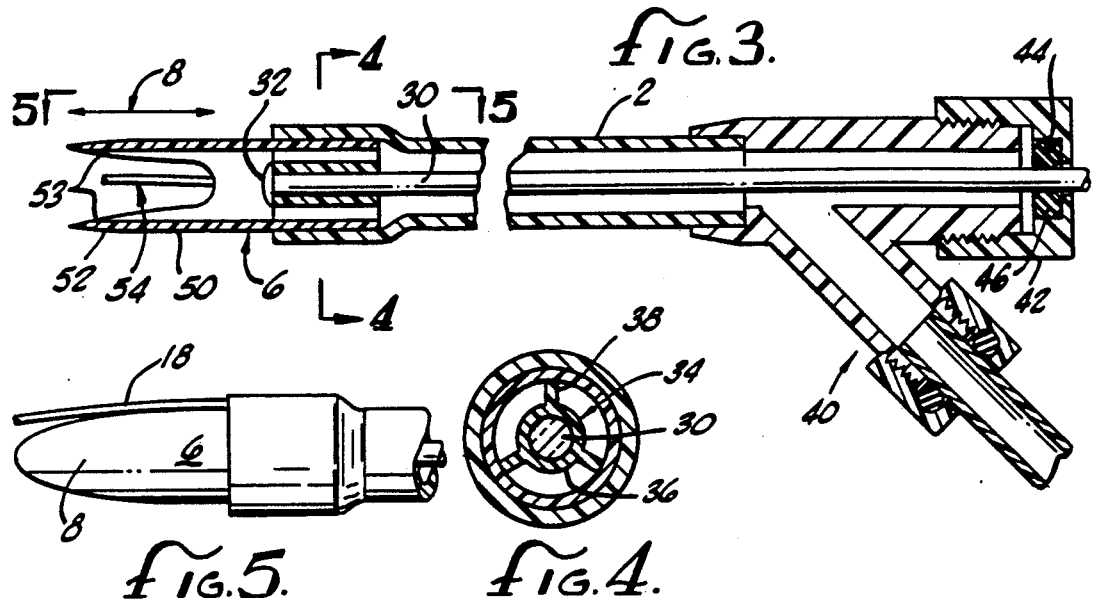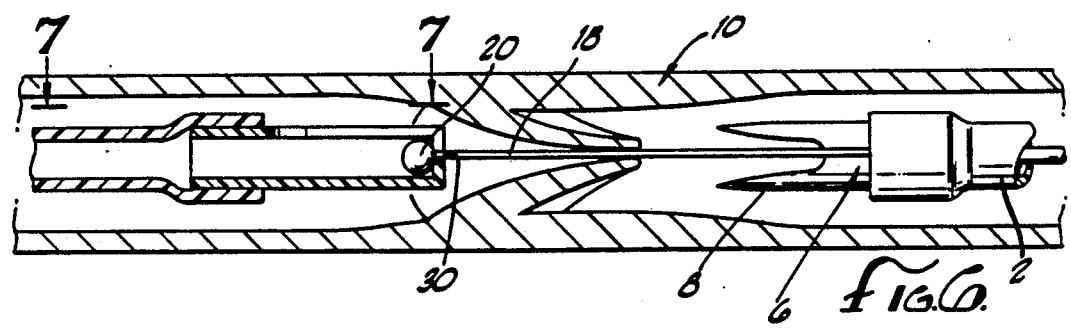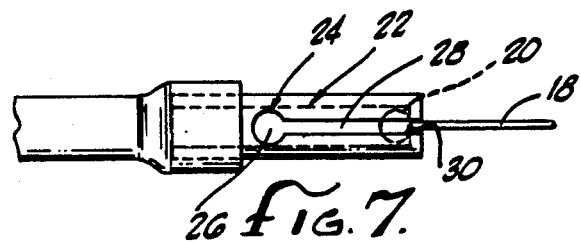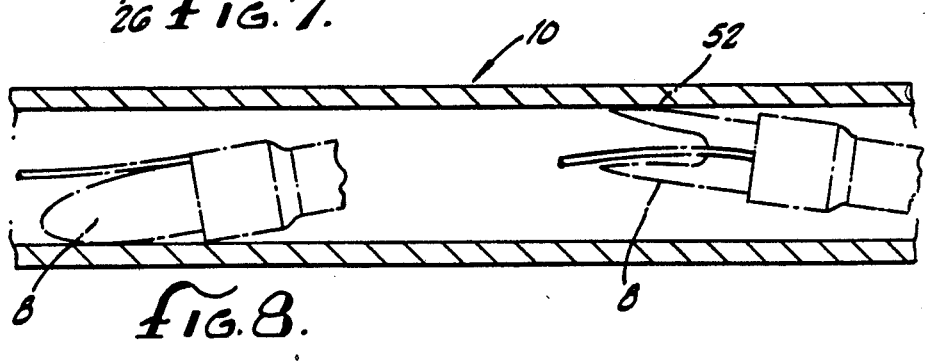

APPARATUS FOR IN-SITU CUTTING OF VALVES WITHIN VEINS AND METHOD THEREFOR

BACKGROUND OF THE INVENTION

This invention relates to a method and apparatus for cutting valves within veins, specifically, for cutting out vein valves during vascular reconstructive surgery. In particular, it constitutes an apparatus for cutting the valves in a vein in a procedure known as in-situ saphenous vein bypass.

In-situ saphenous vein bypass is a procedure which utilizes the saphenous vein in the human leg, which normally returns blood from the ankle upwardly through the leg, to take over the function of the main artery in the leg after it has become too occluded or otherwise impaired to transport the flow of blood required of it. When the saphenous vein is to be used to take over the function of the artery, it becomes necessary to cut open a series of one-way valves in the vein which, in normal functioning, prevent reverse flow of the blood.

Various valve strippers have been developed over the years for performing this function. Some of these valve strippers have used a valve cutter which is passed through the vein in a direction reverse to the normal direction of blood flow to sever the valves. Examples of such valve cutters include the LaMaitre valvulotome made by Vascutech, Inc. of Massachusetts; the Hall vein stripper made by Cabot Ltd. of High Wycombe, England and the Leather valve cutter made by American V. Mueller of Chicago, Ill. These valve strippers operate blind, that is to say they are passed through the vein without direct observation inside the vein of the positioning of the cutters as they operate. While these devices can perform quite satisfactorily in the hands of an experienced cardiovascular surgeon operating on a vein which does not have complications, blind incision of the valves has serious risks. If the cutter's path veers off course into the side wall, as can happen without the ability to observe it directly, the blades can cut the delicate endothelial lining of the vein with serious adverse consequences. Side branches, i.e., veins entering the main vein from the side, may be caught by the valve cutter and torn open also causing serious injury.

To overcome the disadvantages of blind procedures for cutting the vein valves, an apparatus and method have been devised to view the cutter internally of the vein as it travels by using a fiber optic scope. Such an arrangement is disclosed in Chin et al. U.S. Pat. No. 4,768,508. The Chin patent, in one of its embodiments, discloses a pulling catheter which is inserted into the vein near the ankle, and is passed in the normal direction of blood flow through the saphenous vein and the vein valves until its tip emerges through an exit opening created in the vein. A cutting catheter, which carries a group of four cutting fingers at its end, is attached to the pulling catheter which is then pulled reversely through the vein to cause the cutting fingers to cut through the valves. Each cutting finger is V-shaped with its apex facing the vein sidewall. To enable the surgeon to make observations of the vein during the passage of the cutting catheter along it and to visualize the cutting of each valve, a fiber optic scope is mounted in the cutting catheter for viewing through its advanced, open end.

The apparatus disclosed in the Chin patent has special features. To connect the two catheters together, a wire passes through the length of the pulling catheter and has a V-folded hook at leading end. A button at the opposite end of the wire can be pushed inwardly of the pulling catheter to project the hook to grip a flexible loop attached to the adjacent end of the cutting catheter and then retracted to secure the loop against release. To protect the wall of the vein against gouging by the prong-like cutting fingers during passage through it, a retractably mounted sheath surrounds the cutting catheter. The sheath is advanced along the cutting catheter to enclose the cutting fingers during passage through the vein and is withdrawn from the fingers to expose them only during the cutting of a valve.

While the Chin device is generally satisfactory for the purposes for which it is intended, there are respects in which need exists for improvement. With the arrangement of a retractable hook and loop used in the Chin apparatus for linking the two catheters together, the button for moving the wire hook and the loop on the second catheter are separated by the length of the patient's leg during the performance of the operation. This separation complicates the manipulation of the parts necessary to achieve connection of the catheters. The manipulation back and forth of the slidable sheath also adds a level of complication in operating the apparatus that it would be desirable to eliminate. Also, as the device is advanced between valves with the sheath in the shielding position, the sheath can impair the field of view of the optic scope making it more difficult to observe and avoid side branches.

SUMMARY OF THE INVENTION

The present invention constitutes a method and apparatus for in-situ cutting of valves within veins designed to solve the problems that have been discussed.

The invention uses two catheters, each of sufficient flexibility to follow the contour of the vein when passed through it. Entry and exit openings are made in the vein, with the exit opening spaced downstream of the entry opening in the normal direction of blood flood. One of the catheters, the cutting catheter, carries cutting blades. The other, pulling catheter is introduced to the vein through the entry opening, passed through the vein until it emerges through the exit opening, and is then connected to the cutting catheter. The connection is effected by a filament. The filament, which is secured to the cutting catheter, carries a detent which is releasably engagable with a retainer immovably secured to the pulling catheter. The retainer has a keyhole-shaped slot having a wide head opening which accepts the detent and filament and a narrower slit into which the filament passes with the detent being trapped so that the catheters are connected. This arrangement provides a connection which may be rapidly and easily made by the surgeon in the course of the operation with the minimum of manipulation or inconvenience yet which is secure against detachment as the operation proceeds.

The cutting blades, which are diametrically spaced, are sized and shaped to engage and cut through the valve cusps when they are aligned with them and pulled reversely through the valve. Each cutter blade has a rounded nose portion which, if the cutter blade glances against the side of the vein wall, steers the cutter in the direction of the interior of the vein to reduce the risk of gouging the vein wall and damaging the endothelial lining.

The use of the cutter proceeds under observation through a fiber optic viewing scope. The scope is positioned within the bladed catheter for viewing the blades and the adjacent regions of the vein and valves during the cutter's progress reversely through the vein. As each valve is approached and observed through the scope, the catheter carrying the cutting blades can be rotated, if necessary, to align the cutting blades with the cusps of the valve so that the valve is cut open when the cutter is pulled reversely through it. Due to the use of cutters which are alignable to engage the valve cusps under the observation available from the viewing scope and contoured to minimize gouging the vein wall, the present invention eliminates any need for the complexities of movable structure to sheath and unsheath the blades.

An additional significant feature of the invention is that the viewing scope is detachably mounted in the cutting catheter which is disposable. The mounting includes a plurality of spacing members concentrically secured around the scope, spaced along its length, and providing channels through which saline can be selectively passed through the catheter. The saline is used to irrigate the field of view of the scope and back pressure the valves to close them. After an operation, the relatively expensive scope can be withdrawn from the cutting catheter for repeated use, allowing the disposable catheter to be disposed of.

These and other advantages of the invention are further described in the detailed description which follows:

BRIEF DESCRIPTION OF THE DRAWINGS

An apparatus for the in-situ cutting of the valves within veins, constructed in accordance with the preferred embodiment of the invention, for carrying out the preferred method, is illustrated in the accompanying drawings in which:

FIG. 3 shows a fragmentary cross-sectional view of the cutting catheter shown in FIG. 1;

FIG. 4 is a cross-sectional end view of the cutting catheter shown in FIG. 3 taken along the lines 4—4 therein, illustrating a spacer for supporting a fiber optic scope within the cutting catheter;

FIG. 5 is a side view of a cutting blade projecting from the end of the cutting catheter and a filament attached to the cutting catheter;

FIG. 6 constitutes a side view of the cutting catheter and the pulling catheter joined together by the filament, with the cutting catheter approaching a pair of valve cusps;

FIG. 7 is an enlarged view showing the connection of the filament to the pulling catheter, taken along the lines 7—7 in FIG. 6; and FIG. 8 is a cross-sectional view showing the position of the cutting blades in phantom line to illustrate how they are shaped to avoid gouging into the side wall of the vein in the event of a glancing contact with it.

DESCRIPTION OF THE PREFERRED EMBODIMENT

Figures 1, 2A, 2B, 2C:
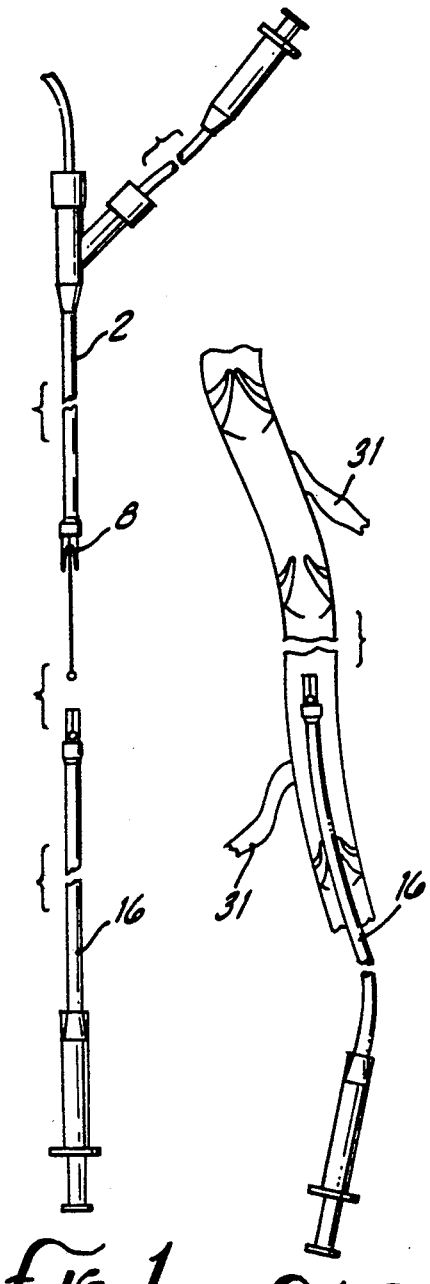
FIG. 1 is an external view of a cutting catheter and a pulling catheter, forming parts of an apparatus constructed in accordance with the preferred embodiment of the invention.
FIGS. 2a-2c illustrate a sequence of steps in performing the preferred embodiment of the method of the present invention in which (i) the pulling catheter shown in FIG. 1 is introduced into the vein and passed through it in the normal direction of blood flow (FIG. 2a); (ii) after the pulling catheter has emerged through an exit opening in the vein, the cutting catheter is connected to it by a filament (FIG. 2b), and; (iii) the catheters are pulled reversely through the vein to cause the cutter blades to cut through the vein valves (FIG. 2c)

An apparatus for in-situ cutting of valves within the saphenous vein, constructed in accordance with a preferred embodiment of the apparatus, is shown in FIG. 1. This procedure is performed to cut through the one-way valves in the saphenous vein to function as an artery to convey blood down the leg.

The apparatus includes a cutting catheter 2, so called because it has a head 6 with cutter blades 8 mounted in its leading end (FIGS. 1 and 3). Valve cutting is performed by moving the cutting catheter 2 through a vein 10 (FIG. 2c) in a direction reverse to the normal direction in which blood flows through the vein so that the blades 8 cut through the one way leaflet valves 12 within the vein. Each valve has two valve cusps 14 with diametrically spaced regions of attachment to the vein. The cusps extend across the vein into contact with each other to act as one way valves, opening when blood flows in the normal direction along the vein, from ankle upwards, and closing to prevent reverse blood flow. The anatomy of the valves in the saphenous vein is illustrated, for example, in the "Atlas of Vascular Surgery" by Zarins and Gewertz (published by Churchill Livingstone 1989) at page 165.

To move the cutting catheter 2 through the valves, a pulling catheter 16 is connected to it and pulled reversely through the vein (FIG. 2c). Both catheters 2 and 16 are sufficiently flexible to follow the contour of the saphenous vein. In the preferred embodiment, the catheters 2 and 16 are model ov.246 catheters made by Nobles-Lai Engineering, Inc., Santa Ana, Calif. in two sizes having external diameters of 2.5 and 2.0 mm. and an internal diameter of 2.0 and 1.5 mm, respectively, fabricated from polyvinyl chloride and polyethylene. However, those skilled in the art will recognize that other catheters sized to fit within the saphenous vein and possessing comparable qualities of stiffness, flexibility and medical inertness may be used.

Of particular interest to the present invention is the procedure by which the catheters are introduced into the vein, are connected, and are then manipulated to cut through the valves. This procedure is illustrated in FIGS. 2a-2c. The pulling catheter 16 is inserted into the saphenous vein through an entry opening (not shown) made in the vein by the surgeon in the region of the patient's ankle. The catheter 16 is then passed upwardly through the saphenous vein, as shown in FIG. 2a, in the normal direction of blood flow, opening and passing through the valves 12 as it travels. Its advancing end eventually emerges through an exit opening (not shown) made by the surgeon downstream of the entry opening, in the region of the patient's groin, as shown in FIG. 2b. The length of the pulling catheter 16 is sufficient that at, its lower end, it is still extending through the entry opening. The catheters are then connected by a linkage, after which pulling force is applied to the end of the pulling catheter still outside the entry opening to pull the cutting catheter 2 reversely through the vein so that the blades 8 can cut through the valves.

Significant advantages of the present invention flow from the linkage which is used to connect the cutting catheter 2 to the pulling catheter 16. As shown in FIG. 2b, the end of the catheter 2 carrying the cutting blades 8 is moved close to the end of the pulling catheter 16 projecting from the exit opening in the vein. The cutting catheter has a filament 18 fixedly secured to it (FIGS. 5 and 6). The filament 18 is a thin, stranded nylon cord, or other medically suitable material, having a sufficiently high tensile strength that it will not break during the pulling of the catheters through the vein. In the preferred embodiment, the filament is injection molded nylon manufactured by Nobles-Lai Engineering, Inc., Santa Ana, Calif. A ball-shaped plastic detent 20 (FIG. 6) is fixed to the filament 18. In the preferred embodiment, the ball has a diameter of 0.85 mm and is made of injection molded nylon.

The detent is releasably engaged with a retainer 26 that is immovably mounted in the end of the pulling catheter 16. In the preferred embodiment, the retainer 22 is a cylindrical tube adhesively secured in the end of the pulling catheter 16 which it distends. The tube has a cylindrical side wall and a flat end wall facing outwardly of the catheter. There is a keyhole-shaped slot 24 through the side wall. The slot 24 has a head opening 26 sized to closely receive the ball 20 and a relatively narrower slit 28 which extends through the cylinder side wall sized to closely receive the filament. The slit also extends through the end wall to its center.

To connect the two catheters, the surgeon simply has to press the ball 20 through the opening 26 in the sidewall of the cylindrical retainer 22 and then slide the filament along the slit 28 to the closed end 30, thereby trapping the detent within the retainer. Once secured, it requires deliberate and careful manipulation later to release the detent. It is virtually impossible for the filament to become inadvertently detached from the retainer during in-situ movements of the catheters through the vein. The just described structure for linking the two catheters together offers significant advantages. The connection can be easily and swiftly made by the surgeon since the only moving part is the detent which slides in the keyhole-shaped slot and this requires little manipulation.

Observation of the cutter blades in relation to the sidewalls of the vein and the valves 12 as the cutters travel are made through a fiber optic viewing scope 30 mounted in the cutting catheter 2, illustrated in FIG. 3. The scope has a field of view through the open ends of the catheter 2 and the head 6 and through an unobstructed space between the cutting blades 8. The fiber optic scope 30 is of the lighted type manufactured by Edwards Laboratories of Santa Ana, Calif. The scope has a central monolithic viewing strand enclosed by illuminating strands. The scope includes a collecting lens 32 at its leading end and, at its opposite end, the scope is secured to a suitable viewing device such as an eyepiece or video viewer (not shown). The viewing scope permits the surgeon to make observations as the cutter blades pass through the saphenous vein to avoid damage to the endothelial lining and to detect side branches 31 so that they are not incised by the cutters. Other regions or structures within the vein, which should be avoided by the cutter blades to prevent injury, can also be detected in time to avoid incision by observation through the scope.

A spacer 34 (FIG. 4) mounts the end of the scope 30 concentrically within the head 6 for viewing through the end of the catheter through an unobstructed space between the cutting blades 8. The spacer 34 has an annular body 36 snugly encircling the fiber optic scope 30 in contact with the lens 32. Three radially projecting legs 38 spaced, symmetrically about the body, extend from it into abutting contact with the interior surface of the cutting head 6. Similar spacers (not shown), but with legs sized to fit the interior diameter of the catheter 2, extend along its length to support the scope 30 in concentric, spaced relation within the catheter. The passage, through the catheter and the spaces between the legs of the spacers, provides a continuous channel between the catheter and the scope for passage of saline into and through the head. The saline is introduced through a Y-junction fitting 40, (FIG. 3) connected to the trailing end of the catheter 2. At the axial end of the Y-junction there is an end cap 42 having a central opening which includes a recessed seat for an O-ring 46. The O-ring supports, and provides a liquid tight seal around, the fiber optic scope 30 which passes through the seal and extends to the eyepiece. The saline is injected to irrigate blood away from the viewing area so that the adjacent regions of the vein may be clearly observed. The injected saline is also used to apply reverse pressure to the cusps of each valve 12 to close it, before the cutting blades cut through the valve, to ensure that the valve is efficiently cut through.

Another aspect of the invention resides in utilizing cutter blades which are shaped and positioned to optimally cut through the valves when they are aligned with the valve cusps by using the scope to enable the requisite rotation of the bladed catheter needed for alignment. Referring to FIGS. 3 and 5, the cutter head is a cylindrical one-piece structure molded from a plastic capable of having sharp edges formed in it, such as high density injection molded nylon. The cutting head is adhesively secured into the open end of the cutting catheter 2 which it distends (FIG. 3). The cutter blades are sized appropriately for the vein which is to be the subject of the valve cutting procedure. Each cutter blade 8, in plan, is generally parabola shaped (FIG. 5). In profile, each blade 8 has a base region 50 (FIG. 3) of the same diameter as the remainder of the cutting head and a nose region 52 which has a gentle inward curve extending to the tip of the blade. The blades have sharp interior edges 53 which are configures to define a slot 54 extending transversely through the cutting head. The slot resembles a U at its apex with the sides of the U flaring outwardly to intersect the tips of the cutting blades.

The inward curve on the outer surface on the nose 52 reduces the risk of damage to the endothelial lining of the vein sidewall in the event of glancing contact between the blade and the vein. By a glancing contact is meant one in which the blade moves against the vein side wall at angle of less than about 15°. Impacts at greater angles of misalignment are less likely because of the observations made through the scope and because the generally parallel alignment of the vein, the catheters and the filament urge the cutter blades to a disposition generally parallel to the vein. As a result, such inadvertent impacts as do occur are more likely to be of the glancing variety. The effect of the curve, as shown on the right side of FIG. 8 is to exert a self-centering effect which protects the vein sidewall rather than damaging it in the event of a glancing impact. A similar self-centering effect occurs if a glancing impact occurs between the cutter blade and the vein side wall with the blade oriented to bring its parabolic edge against the vein, as shown on the left hand side of FIG. 8.

The cutting blades should be aligned with the valve cusps as they approach a valve to be cut through. As the surgeon makes observations through the viewing scope he is able to visualize the blades and their relative alignment to the cusps of the approaching valve. By rotating the cutting catheter, if there is misalignment, the surgeon can align the cutting blades with the valve cusps to achieve effective cutting. An advantage of the cutter blade structure described in conjunction with the ability provided by the scope to visualize the valves and rotate the cutter blades into alignment with the cusps is that there is no need for sheathing and unsheathing the blades as the apparatus is used. With the present invention, the cutter blades are continuously exposed throughout the travel of the cutting blades through the saphenous vein.

A further advantage of the present invention is that the fiber optic viewing scope 30 is detachably connected to the catheter 42 and the Y-junction 40. A fiber optic viewing scope is a relatively expensive piece of equipment. With the present invention, the fiber optic scope is detached after an operation and the remaining parts of the apparatus can be discarded as a disposable. In this manner, the scope can be saved for repeated use with disposable catheters that are used only for a single operation.

In the preferred embodiment of the invention thus far described, movement of the cutting catheter through the vein has been effected by applying a reverse pull using the pulling catheter. In an alternative embodiment of the invention, however, there may be occasions when the cutting catheter, equipped with the viewing scope as described, can be utilized without the pulling catheter. A pushing force is applied directly to the catheter to force the cutter blades reversely through the valves to cut through the valve cusps, using observation of the scope and rotation of the catheter to align the cutters with the valve cusps. This alternative embodiment may be used, for example, when the cutting catheter is to be moved through only a relatively short section of the vein. In this situation, the length of the catheter may be sufficiently short that it possesses sufficient stiffness in compression to permit the blades to perform their cutting function without necessity for applying a pulling force through use of a pulling catheter.

Although the invention has been described with respect to a preferred embodiment and an alternative embodiment, it will be appreciated that modifications that would be obvious to a person of ordinary skill in the pertinent art may be made without departing from the invention defined in the appended claims.

I claim:

1. An apparatus for the in-situ cutting of valves within a vein when pulled reversely through the vein, the valves having valve cusps extending from diametrically spaced regions attachment to the vein into contact with each other to open and permit flow of blood in a normal direction through the vein but closing together to prevent reverse flow, the apparatus comprising,
    a cutting catheter sufficiently flexible to follow the contour of the vein when passed through it, having,
        a cylindrical cutting head secured within an open end of said catheter, said cutting head comprising support means having an opening for mounting a viewing scope therein,
        a pair of cutting blades secured to one end of said cutting head, said blades having sharp cutting edges and being shaped to engage and cut through the valve cusps when the cutting blades are aligned therewith, said blades having exterior sides which are contoured to generally follow the curvature of the interior walls of the vein, said blades being disposed relative to said opening in said support means to provide an unobstructed space for viewing interior sides of the blades,
    a pulling catheter sufficiently flexible to follow the contour of the vein when passed through it,
    linkage means for releasably connecting said catheters, said linkage means including,
        a filament fixed at one of its ends to said one end of said cutting catheter,
        a detent secured to said filament adjacent its other end,
        retaining means immovably attached to said pulling catheter for releasably engaging the detent; and
    a viewing scope mounted within the opening in the support means of said cutting catheter to view through the space between said blades, said scope having a field of view of said blades and the adjacent regions within the vein to enable said cutting catheter to be rotated as necessary to align said cutting blades with the valve cusps.

2. An apparatus as defined in claim 1 wherein said cutting catheter and said cutting blades are designed for disposable one-time use, and wherein the support means releasably supports said viewing scope within said cutting catheter, thereby enabling said scope to be removed from said cutting catheter for reuse before said catheter is disposed of.

3. An apparatus as defined in claim 1 wherein,
    said detent comprises a ball, and
    said retaining means comprises,
        a wall fixedly secured to said unbladed catheter having a keyhole shaped slot, said slot having
            a head opening adjacent the end of said catheter, and
            a slit narrower than said head opening extending longitudinally therefrom, said head opening and said slot being sized to closely receive said ball and said filament, respectively,
        said ball being passed through said head opening and becoming trapped on the opposite side of said wall with said filament extending through said slit to connect said catheters.

4. An apparatus as defined in claim 3 wherein said wall constitutes a tube thereby causing said detent to be housed within the tube interior when said detent is passed through said head opening in said keyhole-shaped slot.

5. An apparatus as defined in claim 4 further having an end wall secured to said tube, said narrow slit extending through said end wall to about the center thereof, said detent pressing against said end wall as the force is applied to the pulling catheter to move said catheters through the vein.

6. An apparatus as defined in claim 1 wherein each said cutting blade has,
    an external contour, viewed in a plan direction perpendicular to the major outer surface of the blade, which has a rounded tip extending in a parabola-like shape to blend with the cylindrical outer surface of said cutting head,
    an outer edge, viewed side on relative to the plan view, which is flush with the cylindrical outer surface of said cutting head except for a region adjacent the tip which is curved radially inwardly to reduce the risk of gouging the vein in the event of a glancing contact with the vein side wall, and a cutting edge extending from said tip axially and radially inwardly within said cutting head, said cutting edges of said cutting blades together defining a generally U-shaped opening extending transversely and without obstruction through said cutting head.

7. An apparatus for the in-situ cutting of valves within a vein when moved reversely through the vein, the valves having valve cusps extending from diametrically spaced regions of attachment to vein into contact with each other to open and permit flow of blood in a normal direction through the vein but closing together to prevent reverse flow, the apparatus comprising, a catheter sufficiently flexible to follow the contour of the vein when passed through it, a cutting head having, a generally cylindrical body secured to and extending longitudinally from one end of said catheter, a pair of cutting blades integral with said body projecting longitudinally and disposed around a periphery of said body to provide a viewing space between the blades, each said cutting blade having sharp cutting edges and comprising, an external contour, viewed in a plan direction perpendicular to the major outer surface of the blade, which has rounded tip extending in a parabola-like shape to blend with the outer surface of said cylindrical body, an outer profile, viewed side on relative to the plan view, which is generally flush with the cylindrical outer surface of said body except for a curved radially inwardly curved nose region adjacent the tip to reduce the risk of gouging the vein side wall in the event of a glancing contact with it; and a cutting edge extending from said tip axially and radially inwardly from said tip, said cutting edges of said opposed cutting blade defining a generally U-shaped opening having a bell-like flare at its outer end, said cutting edges cutting through the valve cusps when aligned therewith and pulled reversely through the valve; and a viewing scope mounted within said catheter to view through the viewing space between said blades, said scope having a field of view of said blades and the adjacent regions within the vein to enable said catheter to be rotated as necessary to align said cutting blades with the valve cusps.

8. A method for the in-situ cutting of valves within a vein, the valves having valve cusps extending from diametrically spaced regions of attachment to the vein into contact with each other to provide contacting portions which open to allow blood flow in a normal direction through the vein and which close to prevent reverse flow, the method comprising the steps of, making entry and exit openings in the vein, with the exit opening spaced downstream of the entry opening in the normal direction of blood flow;

introducing a pulling catheter into the vein through the entry opening and passing the pulling catheter through the vein and valves such that one end of the pulling catheter emerges through the exit opening, attaching said one end of the pulling catheter to an end of a cutting catheter and applying force to another end of the pulling catheter to move cutting blades on the cutting catheter through the vein to a location proximate to a valve within the vein, making observations through the viewing scope of the blades in relation to the vein wall and the valves, positioning nose portions of the blades within respective valve cusps of said valve such that slot portions of the blades receive the contacting portions of the valve cusps, and applying force to said another end of the pulling catheter to cut the valve.

9. A method as defined in claim 8 wherein the step of attaching comprises, passing a detent, attached to one of the catheters by a filament, through an opening in a retainer tube on the other of the catheters, sliding the detent away from the opening towards an end of the tube, said step of sliding the detent comprising sliding the filament through a slot in the tube which is narrower than the detent such that the filament extends from said tube with said detent captured therein.

10. A method, as defined in claim 8, additionally comprising the step of rotating the cutting catheter to position the nose portions of the cutting blades within the valve cusps.

11. An apparatus for the in-situ cutting of a valve within a vein, said valve comprising a pair of valve cusps having portions which contact each other to form a flow path, comprising:

a cutting catheter comprising a cutting head having sharp cutting edges disposed around the periphery of the cutting head to provide a central viewing space between said cutting edges for viewing the interior of said vein, said head comprising a support for mounting a viewing scope to provide viewing through said viewing space, said cutting edges contoured to form a pair of nose regions with a pair of slot regions therebetween, said slot regions sized to receive contacting portions of said valve cusps when said nose regions are inserted into respective valve cusps of said valve; and a pulling catheter for attaching to said cutting catheter.

12. An apparatus for in-situ cutting of a valve within a vein, comprising:

a cutting catheter comprising a cutting head having cutting edges following a continuous, closed path around a periphery of said cutting head, said cutting edges being substantially equidistant from a central longitudinal axis of said cutting head and forming an open space therebetween, whereby said cutting edges cleanly cut said valve around the entire periphery of said valve without ripping or tearing said valve, said cutting head further comprising a mount for mounting a viewing scope to view said open space; and a pulling catheter for pulling said cutting catheter through said vein, said cutting edges oriented to cut said valve in response to application of a pulling force on said pulling catheter.

* * * * *